(12) United States Patent
Hwang et al.

(10) Patent No.: US 12,134,740 B2
(45) Date of Patent: *Nov. 5, 2024

(54) APPARATUS FOR PRODUCING AROMATIC HYDROCARBONS

(71) Applicant: LG CHEM, LTD., Seoul (KR)

(72) Inventors: Sung June Hwang, Daejeon (KR); Tae Woo Kim, Daejeon (KR); Sung Kyu Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 653 days.

This patent is subject to a terminal disclaimer.

(21) Appl. No.: 17/430,667

(22) PCT Filed: Nov. 9, 2020

(86) PCT No.: PCT/KR2020/015571
§ 371 (c)(1),
(2) Date: Aug. 12, 2021

(87) PCT Pub. No.: WO2021/256622
PCT Pub. Date: Dec. 23, 2021

(65) Prior Publication Data
US 2022/0306951 A1    Sep. 29, 2022

(30) Foreign Application Priority Data

Jun. 16, 2020   (KR) .................. 10-2020-0072915
Oct. 28, 2020   (KR) .................. 10-2020-0140998

(51) Int. Cl.
*C10G 67/02*     (2006.01)
*B01D 3/14*      (2006.01)
(Continued)

(52) U.S. Cl.
CPC .............. *C10G 67/02* (2013.01); *B01D 3/143* (2013.01); *B01D 3/40* (2013.01); *B01J 19/245* (2013.01);
(Continued)

(58) Field of Classification Search
CPC . B01D 3/00; B01D 3/14; B01D 3/143; B01D 3/34; B01D 3/40; B01J 19/00; B01J 19/24; B01J 19/245; B01J 2219/00; B01J 2219/00002; B01J 2219/00027; B01J 2219/0004; C07C 7/00; C07C 7/04;
(Continued)

(56) References Cited

U.S. PATENT DOCUMENTS 3,304,340 A   2/1967   Noll
4,097,371 A   6/1978   Giroux
(Continued)

FOREIGN PATENT DOCUMENTS

| CN | 101208409 A | 6/2008 |
|---|---|---|
| CN | 209555160 U | 10/2019 |
| JP | 4521656 B2 | 8/2010 |
| JP | 2011-137032 A | 7/2011 |
| JP | 2012-509976 A | 4/2012 |
| KR | 10-0645659 B1 | 11/2006 |
| KR | 10-2008-0084746 A | 9/2008 |
| KR | 10-2013-0034821 A | 4/2013 |

(Continued)

*Primary Examiner* — Natasha E Young
(74) *Attorney, Agent, or Firm* — Bryan Cave Leighton Paisner LLP

(57) ABSTRACT

An apparatus for producing aromatic hydrocarbons including: a C6 separation column; a C7 separation column; a first gasoline hydrogenation unit; a C8 separation column; an extractive distillation column; a hydrodealkylation reaction unit; and a second gasoline hydrogenation unit.

14 Claims, 2 Drawing Sheets

(51) Int. Cl.
*B01D 3/40* (2006.01)
*B01J 19/24* (2006.01)
(52) U.S. Cl.
CPC . *B01J 2219/0004* (2013.01); *C10G 2300/202* (2013.01); *C10G 2400/30* (2013.01)
(58) Field of Classification Search
CPC ......... C07C 15/00; C07C 15/02; C07C 15/04; C07C 15/06; C07C 15/067; C07C 15/08; C07C 15/40; C07C 15/42; C07C 15/44; C07C 15/46; C10G 7/00; C10G 7/08; C10G 65/00; C10G 65/02; C10G 65/12; C10G 65/14; C10G 65/16; C10G 67/00; C10G 67/02; C10G 69/00; C10G 69/02; C10G 69/06; C10G 2300/00; C10G 2300/20; C10G 2300/201; C10G 2300/202; C10G 2300/40; C10G 2300/4006; C10G 2400/00; C10G 2400/30
See application file for complete search history.

(56) References Cited

U.S. PATENT DOCUMENTS

| | | |
|---|---|---|
| 2004/0055933 A1 | 3/2004 | Groten |
| 2012/0067776 A1 | 3/2012 | Diehl et al. |
| 2019/0055483 A1 | 2/2019 | Bafna |
| 2019/0338202 A1* | 11/2019 | Pigourier ................ B01J 19/24 |
| 2022/0306555 A1* | 9/2022 | Hwang ................... C07C 15/04 |

FOREIGN PATENT DOCUMENTS

| | | |
|---|---|---|
| KR | 10-2015-0066586 A | 6/2015 |
| KR | 10-2016-0124871 A | 10/2016 |
| KR | 10-2017-0018426 A | 2/2017 |
| KR | 10-2020-0062553 A | 6/2020 |
| TW | M594605 U | 5/2020 |
| WO | 2016/011521 A1 | 1/2016 |
| WO | 2019-105767 A1 | 6/2019 |

* cited by examiner

【FIG. 1】
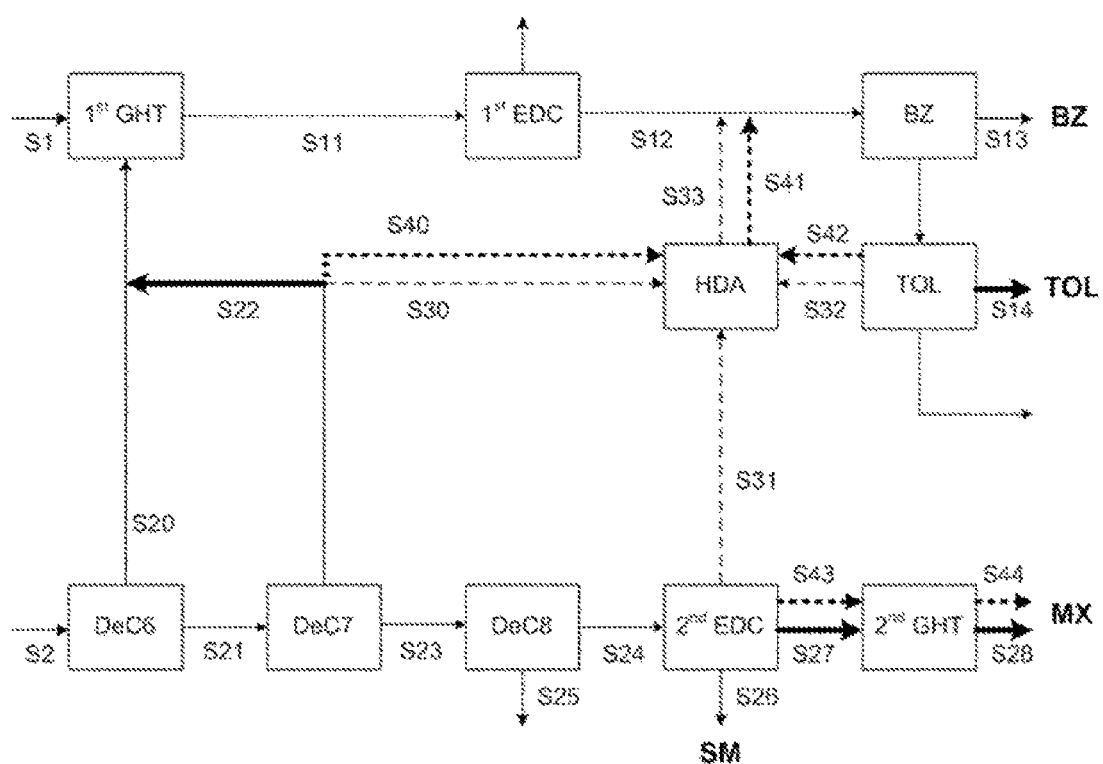

[FIG. 2]
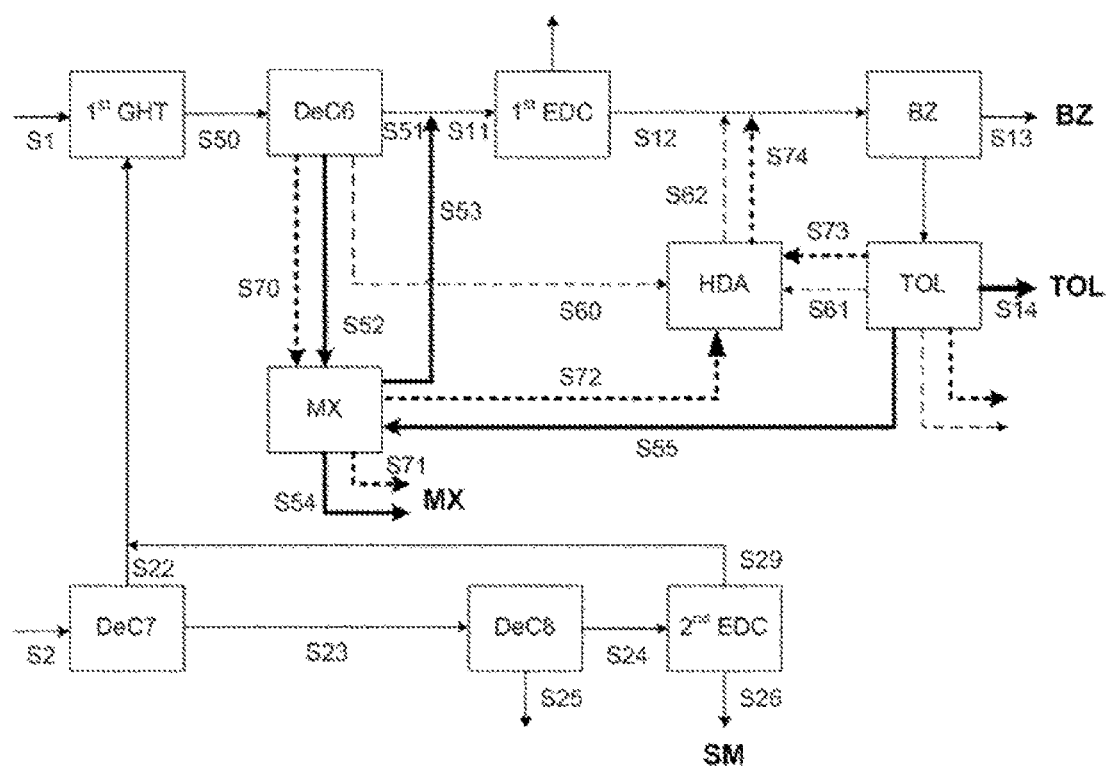

APPARATUS FOR PRODUCING AROMATIC HYDROCARBONS

CROSS-REFERENCE TO RELATED APPLICATIONS

This application is a U.S. national stage of international application No. PCT/KR2020/015571, now WO 2012/256622, filed on Nov. 9, 2020, and claims the benefit of priority to Korean Patent Application No. 10-2020-0072915 filed on Jun. 16, 2020, and Korean Patent Application No. 10-2020-0140998 filed on Oct. 28, 2020, the entire contents of which are incorporated herein as a part of the specification.

TECHNICAL FIELD

The present invention relates to an apparatus for producing aromatic hydrocarbons, and more particularly, to an apparatus which may be operated in a first mode, a second mode, or a third mode to selectively produce styrene and also, if necessary, desired BTX components.

BACKGROUND

A naphtha cracking center (hereinafter, referred to as "NCC") is a process of pyrolyzing naphtha, which is a fraction of gasoline, at a temperature of about 950° C. to 1,050° C. to produce ethylene, propylene, butylene, and benzene, toluene, and xylene (BTX), and the like which are basic raw materials of petrochemical products.

Conventionally, raw pyrolysis gasoline (RPG), which is a by-product of a process of producing ethylene and propylene using naphtha as a raw material, was used to produce benzene, BTX, and styrene in separate processes.

The process of producing benzene was performed by largely including a gasoline hydrogenation (GHT, hydrodesulfurization) process, a prefraction (PF) process, an extractive distillation process (EDP), and a hydrodealkylation (HDA, dealkylation) process using an RPG raw material stream. In this case, the raw material is supplied to gasoline hydrogenation (GHT) without separating C7+ hydrocarbons from a raw material stream, thereby increasing an amount of hydrogen used due to an increase in a flow rate supplied to the gasoline hydrogenation (GHT). In addition, after the gasoline hydrogenation (GHT) process, a C6 hydrocarbon and C7+ hydrocarbons are separated, the C7+ hydrocarbons are subjected to hydrodealkylation again and then mixed again to separate benzene, thereby doubling the energy consumption.

In addition, the process of producing BTX was performed by largely including a gasoline hydrogenation (GHT) process, a prefraction (PF) process, and an extractive distillation process (EDP). In this case, the total amount of the raw material stream is supplied to gasoline hydrogenation (GHT), thereby increasing an amount of hydrogen used due to an increase in a flow rate supplied to the gasoline hydrogenation (GHT). In addition, after the gasoline hydrogenation (GHT) process, the prefraction (PF) for separating benzene, toluene, and xylene is performed, which complicates the process. In particular, the process is more complicated in the case of xylene, because the route for producing xylene from C8+ hydrocarbons remaining after separating prefractionated C8+ hydrocarbons, benzene, and toluene is a lengthy one.

In addition, the styrene extractive distillation process is a process of directly producing styrene through an extractive distillation process (EDP) from RPG, and may be positioned at the start of the process of producing benzene or BTX. Here, to separate a C8 hydrocarbon abundant in styrene before supplying the RPG to EDP, a prefraction (PF) process step of fractionating RPG to C7− hydrocarbons, a C8 hydrocarbon, and C9+ hydrocarbons is performed beforehand. However, in this case, because the separated C7− hydrocarbons and C8 hydrocarbon are introduced into a process of producing benzene or BTX and subjected to a gasoline hydrogenation (GHT) process, they are mixed again. After performing the GHT step, the C7− hydrocarbons and the C8 hydrocarbon are separated again in the process of producing benzene or BTX, and as such, performing a step of separating C7− hydrocarbons and a C8 hydrocarbon twice leads to a waste of process costs and energy.

SUMMARY

To solve the problems described in the Background Art, an objective of the present invention is to provide an apparatus for producing aromatic hydrocarbons which may selectively produce styrene and if necessary, BTX, benzene, or benzene and xylene, while simplifying the process and reducing energy.

In one general aspect, an apparatus for producing aromatic hydrocarbons includes: a C6 separation column being supplied with a raw material stream, supplying an upper discharge stream to a first gasoline hydrogenation (hydrodesulfurization) unit, and supplying a lower discharge stream to a C7 separation column; a C7 separation column being supplied with the lower discharge stream from the C6 separation column, and the C7 separation column supplying an upper discharge stream to the first gasoline hydrogenation unit or a hydrodealkylation (dealkylation) reaction unit, and supplying a lower discharge stream to a C8 separation column; a first gasoline hydrogenation unit being supplied with the upper discharge stream from the C6 separation column or the upper discharge stream from the C6 separation column and the upper discharge stream from the C7 separation column to perform a hydrodesulfurization reaction; a C8 separation column being supplied with the lower discharge stream from the C7 separation column, the C8 separation column having a lower discharge stream removed therefrom, and supplying an upper discharge stream to a second extractive distillation column; a second extractive distillation column being supplied with the upper discharge stream from the C8 separation column and the second extractive distillation column supplying an upper discharge stream to a second gasoline hydrogenation unit or the hydrodealkylation reaction unit; a hydrodealkylation reaction unit being supplied with the upper discharge stream from the C7 separation column or the upper discharge stream from the C7 separation column and the upper discharge stream from the second extractive distillation column to perform a hydrodealkylation reaction; and a second gasoline hydrogenation unit being supplied with the upper discharge stream from the second extractive distillation column to perform a hydrodesulfurization reaction.

According to the apparatus for producing aromatic hydrocarbons of the present invention, styrene and also, if necessary, BTX, benzene, or benzene and xylene may be selectively produced, and in this process, a prefraction step which was required for production of BTX or benzene may be omitted to reduce energy due to a decrease in the amount of steam used.

In addition, only a C6– hydrocarbon stream excluding C7+ hydrocarbons in the raw material stream is supplied to a first gasoline hydrogenation unit, thereby decreasing a flow rate supplied to the first gasoline hydrogenation unit to decrease the amount of hydrogen used in the first gasoline hydrogenation unit and increase the catalyst lifetime.

In addition, a prefraction column and a xylene separation column are removed from a conventional BTX production process to simplify the process, and a second gasoline hydrogenation unit is installed to allow xylene to be directly produced from an upper discharge stream from a second extractive distillation column, thereby solving the problem associated with the complicated and long conventional production process for producing xylene.

In addition, the second gasoline hydrogenation unit is installed, whereby an unnecessary process of hydrodesulfurizing an upper discharge stream from a second extractive distillation column in the first gasoline hydrogenation unit and separating it again is not required.

BRIEF DESCRIPTION OF DRAWINGS

FIG. 1 is a flow chart of the apparatus for producing aromatic hydrocarbons according to an exemplary embodiment of the present invention.

FIG. 2 is a flow chart of the apparatus for producing aromatic hydrocarbons according to the Comparative Example.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "stream" may refer to a fluid flow in a process, or may refer to a fluid itself flowing in a pipe. Specifically, the "stream" may refer to both a fluid itself flowing in a pipe connecting each apparatus and a fluid flow. In addition, the fluid may refer to a gas or a liquid.

In the present invention, the term "C# hydrocarbon", wherein "#" is a positive integer, represents all hydrocarbons having # carbon atoms. Therefore, the term "C8 hydrocarbon" represents a hydrocarbon compound having 8 carbon atoms. In addition, the term "C#+ hydrocarbon" represents all hydrocarbon molecules having # or more carbon atoms. Therefore, the term "C9+ hydrocarbon" represents a mixture of hydrocarbons having 9 or more carbon atoms. In addition, the term "C#– hydrocarbon" represents all hydrocarbon molecules having # or fewer carbon atoms. Therefore, the term "C7– hydrocarbon" represents a mixture of hydrocarbons having 7 or fewer carbon atoms.

In the present invention, BTX is an abbreviation of benzene, toluene, and xylene, and the xylene may include ethylene benzene, m-xylene, o-xylene, and p-xylene.

Hereinafter, the present invention will be described in more detail for better understanding of the present invention.

An exemplary embodiment is directed to an apparatus for producing aromatic hydrocarbons. The apparatus for producing aromatic hydrocarbons selectively produces styrene and if necessary, BTX, benzene, or benzene and xylene simultaneously, while the process may be simplified and process energy may be reduced as compared with the case of conventionally producing benzene, BTX, and styrene separately.

Specifically, the conventional process of producing benzene was performed by largely including a gasoline hydrogenation (GHT) process, a prefraction (PF) process, an extractive distillation process (EDP), and a hydrodealkylation (HDA) process using an RPG raw material stream. In this case, the raw material is supplied to gasoline hydrogenation (GHT) without separating C7+ hydrocarbons from a raw material stream, thereby increasing an amount of hydrogen used due to an increase in a flow rate supplied to the gasoline hydrogenation (GHT). In addition, after the gasoline hydrogenation (GHT) process, a C6 hydrocarbon and C7+ hydrocarbons are separated, the C7+ hydrocarbons are subjected to hydrodealkylation again and then mixed again to separate benzene, thereby doubling the energy consumed.

In addition, the conventional process of producing BTX was performed by largely including a gasoline hydrogenation (GHT) process, a prefraction (PF) process, and an extractive distillation process (EDP). In this case, the total amount of the raw material stream is supplied to gasoline hydrogenation (GHT), thereby increasing the amount of hydrogen used due to an increase in a flow rate supplied to the gasoline hydrogenation (GHT). In addition, because the prefraction (PF) for separating benzene, toluene, and xylene is performed after the gasoline hydrogenation (GHT) process, the process is complicated. In particular, in the case of xylene, the process is more complicated because the route for producing xylene from C8+ hydrocarbons remaining after separating prefractionated C8+ hydrocarbons, benzene, and toluene is a lengthy one.

In addition, the conventional styrene extractive distillation process is a process of directly producing styrene through an extractive distillation process (EDP) from RPG, and may be positioned at a start of the process of producing benzene or BTX. A prefraction step of fractionating RPG to C7– hydrocarbons, a C8 hydrocarbon, and C9+ hydrocarbons is performed beforehand to separate a C8 hydrocarbon abundant in styrene before supplying the RPG to the extractive distillation process. However, because separated C7– hydrocarbons and a C8 hydrocarbon is introduced into a process of producing benzene or BTX and subjected to a gasoline hydrogenation process, they are mixed again. After performing the gasoline hydrogenation process step, the C7– hydrocarbons and the C8 hydrocarbon are separated again in the process of producing benzene or BTX, and as such, performing a step of separating the C7– hydrocarbons and the C8 hydrocarbon twice leads to a waste of process costs and energy.

Conventionally, RPG was used to produce benzene, BTX, and styrene in separate processes. In this case, there were problems such as significant plant costs, unnecessary process steps and excessive energy consumption, as described above.

In an exemplary embodiment, a process, which may not be easily technically derived from each conventional process for producing benzene, BTX, and styrene, and may selectively produce BTX, benzene, or benzene and xylene as well as styrene, was designed. In this case, the process was further simplified and a product output compared with an amount of a raw material used was maximized while minimizing a process energy use.

According to an exemplary embodiment of the present invention, the apparatus for producing aromatic hydrocarbons may be described with reference to FIG. 1. As illustrated in FIG. 1, an apparatus for producing aromatic hydrocarbons includes: a C6 separation column (DeC6) being supplied with a raw material stream, and the C6 separation column (DeC6) supplying an upper discharge stream to a first gasoline hydrogenation unit ($1^{st}$ GHT), and supplying a lower discharge stream to a C7 separation column (DeC7); a C7 separation column (DeC7) being supplied with the lower discharge stream from the C6 separation column (DeC6), and the C7 separation column (DeC7) supplying an upper discharge stream to the first gasoline hydrogenation unit ($1^{st}$ GHT) or a hydrodealkylation reaction unit (HDA), and supplying a lower discharge stream to a C8 separation column (DeC8); a first gasoline hydrogenation unit ($1^{st}$ GHT) being supplied with the upper discharge stream from the C6 separation column (DeC6) or the upper discharge stream from the C6 separation column (DeC6) and the upper discharge stream from the C7 separation column (DeC7) to perform a hydrodesulfurization reaction; a C8 separation column (DeC8) being supplied with the lower discharge stream from the C7 separation column (DeC7), and the C8 separation column (DeC8) removing a lower discharge stream, and supplying an upper discharge stream to a second extractive distillation column ($2^{nd}$ EDC); a second extractive distillation column ($2^{nd}$ EDC) being supplied with the upper discharge stream from the C8 separation column (DeC8), and the second extractive distillation column ($2^{nd}$ EDC) supplying an upper discharge stream to a second gasoline hydrogenation unit ($2^{nd}$ GHT) or the hydrodealkylation reaction unit (HDA); a hydrodealkylation reaction unit (HDA) being supplied with the upper discharge stream from the C7 separation column (DeC7) or the upper discharge stream from the C7 separation column (DeC7) and the upper discharge stream from the second extractive distillation column ($2^{nd}$ EDC) to perform a hydrodealkylation reaction; and a second gasoline hydrogenation unit ($2^{nd}$ GHT) being supplied with the upper discharge stream from the second extractive distillation column ($2^{nd}$ EDC) to perform a hydrodesulfurization reaction.

According to an exemplary embodiment of the present invention, the C6 separation column (DeC6) may be supplied with the raw material stream and separated into an upper discharge stream including C6− hydrocarbons and a lower discharge stream including C7+ hydrocarbons. Here, the upper discharge stream from the C6 separation column (DeC6) may be supplied to the first gasoline hydrogenation unit ($1^{st}$ GHT) and the lower discharge stream may be supplied to the C7 separation column (DeC7).

The raw material stream may include raw pyrolysis gasoline (RPG). The raw pyrolysis gasoline may be a by-product of a process producing ethylene, propylene, and the like using naphtha in a unit forming a naphtha cracking center (NCC). The raw material stream may be a C5+ hydrocarbon mixture, specifically a mixture including C5 to C10 hydrocarbons. For example, the RPG may include one or more selected from the group consisting of iso-pentane, n-pentane, 1,4-pentadiene, dimethyl acetylene, 1-pentene, 3-methyl-1-butene, 2-methyl-1-butene, 2-methyl-2-butene, isoprene, trans-2-penstene, cis-2-pentene, trans-1,3-pentadiene, cyclopentadiene, cyclopentane, cyclopentene, n-hexane, cyclohexane, 1,3-cyclohexadiene, n-heptane, 2-methylhexane, 3-methylhexane, n-octane, n-nonane, benzene, toluene, ethylbenzene, m-xylene, o-xylene, p-xylene, styrene, dicyclopentadiene, indene, and indane.

As the C6 separation column (DeC6), a C6 separation column (DeC6) used in the prefraction step in the conventional benzene production process or BTX production process may be reused.

According to an exemplary embodiment of the present invention, the C7 separation column (DeC7) may be supplied with the lower discharge stream from the C6 separation column (DeC6) and separated into an upper discharge stream including a C7 hydrocarbon and a lower discharge stream including C8+ hydrocarbons. Here, the upper discharge stream from the C7 separation column (DeC7) may be supplied to the first gasoline hydrogenation unit ($1^{st}$ GHT) or supplied to the hydrodealkylation reaction unit (HDA), and the lower discharge stream may be supplied to the C8 separation column (DeC8).

According to an exemplary embodiment of the present invention, the C6 separation column (DeC6) and the C7 separation column (DeC7) are provided to selectively produce styrene and, if necessary, BTX, benzene, or benzene and xylene from the raw material stream including C5 to C10 hydrocarbons. Specifically, the raw material stream is subjected to the C6 separation column (DeC6) and the C7 separation column (DeC7) to be separated into C6− hydrocarbons, a C7 hydrocarbon, and C8+ hydrocarbons. Specifically, the raw material stream was supplied to the C6 separation column (DeC6), C6− hydrocarbons were separated from the upper discharge stream from the C6 separation column (DeC6), a C7 hydrocarbon was separated from the upper discharge stream from the C7 separation column, and C8+ hydrocarbons were separated from the lower discharge stream from the C7 separation column. Here, the stream including C6− hydrocarbons may be a stream for producing benzene, the stream including a C7 hydrocarbon may be a stream for producing benzene or toluene, and the stream including C8+ hydrocarbons may be a stream for producing styrene and benzene or styrene and xylene together.

According to an exemplary embodiment of the present invention, the first gasoline hydrogenation unit ($1^{st}$ GHT) may hydrodesulfurize the upper discharge stream from the C6 separation column (DeC6) or the upper discharge stream from the C6 separation column (DeC6) and the upper discharge stream from the C7 separation column (DeC7), in the presence of separately supplied hydrogen and a catalyst. The catalyst separately supplied to the first gasoline hydrogenation unit ($1^{st}$ GHT) may be a catalyst allowing selective hydrogenation. For example, the catalyst may include one or more selected from the group consisting of palladium, platinum, copper, and nickel. In some cases, the catalyst may be supported on one or more supporters selected from the group consisting of gamma alumina, activated carbon, and zeolite.

According to an exemplary embodiment of the present invention, benzene or benzene and toluene may be separated from the discharge stream from the first gasoline hydrogenation unit ($1^{st}$ GHT). Specifically, the discharge stream from the first gasoline hydrogenation unit ($1^{st}$ GHT) is supplied to the first extractive distillation column ($1^{st}$ EDC) and benzene or benzene and toluene may be separated, respectively, from the lower discharge stream from the first extractive distillation column ($1^{st}$ EDC).

The first gasoline hydrogenation unit ($1^{st}$ GHT) may include the first gasoline hydrogenation reactor and the second gasoline hydrogenation reactor. For example, the stream supplied to the first gasoline hydrogenation unit ($1^{st}$ GHT) may be supplied to the first gasoline hydrogenation reactor, the discharge stream from the first gasoline hydrogenation reactor may be supplied to the second gasoline hydrogenation reactor, the discharge stream from the second gasoline hydrogenation reactor may be supplied to the first extractive distillation column ($1^{st}$ EDC), and benzene or benzene and toluene may be separated from the lower discharge stream from the first extractive distillation column ($1^{st}$ EDC). Here, the discharge stream from the second gasoline hydrogenation reactor may be passed through a stripper and then supplied to the first extractive distillation column ($1^{st}$ EDC).

In addition, the first gasoline hydrogenation unit ($1^{st}$ GHT) may further include a separately required device in addition to the first gasoline hydrogenation reactor and the second gasoline hydrogenation reactor. For example, the first gasoline hydrogenation unit ($1^{st}$ GHT) may further include a C5 separation column and the C5 separation column may be disposed between the first gasoline hydrogenation reactor and the second gasoline hydrogenation reactor. Thus, the upper discharge stream from the C6 separation column (DeC6) and the C7 separation column (DeC7) is subjected to the first gasoline hydrogenation unit ($1^{st}$ GHT), while impurities such as a fuel gas (F/G) and a C5 hydrocarbon may be removed.

An operating temperature of the first gasoline hydrogenation reactor may be 50° C. to 200° C., 60° C. to 170° C., or 60° C. to 140° C. The first gasoline hydrogenation reactor is operated at a temperature in the above ranges, thereby performing the hydrogenation reaction in a liquid phase. Specifically, in the first gasoline hydrogenation reactor, the hydrogenation reaction to remove olefins may be performed in a liquid phase at a low temperature. For example, the olefin may be a hydrocarbon having a double bond, and may include styrene and diolefin. The double bond may be broken due to the hydrogenation reaction in the first gasoline hydrogenation reactor to convert the olefin into a saturated hydrocarbon.

An operating temperature of the second gasoline hydrogenation reactor may be 250° C. to 400° C., 280° C. to 360° C., or 280° C. to 320° C. The second gasoline hydrogenation reactor is operated at a temperature in the above ranges, thereby performing the hydrogenation reaction in a gas phase. Specifically, in the second gasoline hydrogenation reactor, residual olefins which have not been removed in the first gasoline hydrogenation reactor are removed and the hydrogenation reaction may be performed in a gas phase for removing sulfur. Thus, the discharge stream from the second gasoline hydrogenation reactor from which olefins and sulfur have been removed may be passed through a stripper without additional prefraction and then supplied to the first extractive distillation column ($1^{st}$ EDC) in a total amount.

As such, in the present application, the total amount of the raw material stream is not supplied to the first gasoline hydrogenation unit ($1^{st}$ GHT) unlike in the conventional art, and C6– hydrocarbons or C7– hydrocarbons in the raw material stream are supplied to the first gasoline hydrogenation unit ($1^{st}$ GHT), thereby decreasing a flow rate supplied to the first gasoline hydrogenation unit ($1^{st}$ GHT) and also not requiring additional separation processes to reduce energy and utility costs.

According to an exemplary embodiment of the present invention, the raw material stream including a C5 hydrocarbon and a C6 hydrocarbon may be separately supplied to the first gasoline hydrogenation unit ($1^{st}$ GHT). Here, the raw material stream supplied to the first gasoline hydrogenation unit ($1^{st}$ GHT) may not include styrene. For example, the raw material stream including C5 and C6 hydrocarbons separately supplied to the gasoline hydrogenation unit ($1^{st}$ GHT) may include one or more selected from the group consisting of cyclopentadiene, pentadiene, isoprene, cyclopentene, 1-pentene, 3-methyl-1-butene, cyclopentane, 2-methyl-butene, normal pentane, benzene, and a C6 non-aromatic hydrocarbon, as the lower discharge stream of a C4 separation column (not shown) in an NCC process. Conventionally, the lower discharge stream from the C4 separation column was mixed with RPG described above and used as the raw material stream of a benzene production process, a BTX production process, and a styrene production process. However, the lower discharge stream from the C4 separation column includes benzene but does not include styrene, and thus, when supplied to the C6 separation column (DeC6), additional unnecessary processes such as separation and mixing may be performed. Thus, in the present invention, the lower discharge stream from the C4 separation column (not shown) is separately supplied to the first gasoline hydrogenation unit ($1^{st}$ GHT) to decrease the flow rate supplied to the C6 separation column (DeC6) and is not subjected to an unnecessary process step to reduce energy.

A content of olefins in the raw material stream separately supplied to the first gasoline hydrogenation unit ($1^{st}$ GHT) may be 40 wt % or more, 40 wt % to 70 wt %, or 40 wt % to 60 wt %.

According to an exemplary embodiment of the present invention, a first extractive distillation column ($1^{st}$ EDC) may be further included. The discharge stream from the first gasoline hydrogenation unit ($1^{st}$ GHT) may be supplied to the first extractive distillation column ($1^{st}$ EDC) and non-aromatic hydrocarbons may be separated from an upper portion and benzene or benzene and toluene may be separated from the lower discharge stream of the first extractive distillation column ($1^{st}$ EDC).

In the first extractive distillation column ($1^{st}$ EDC), benzene or benzene and toluene, which are aromatic hydrocarbons in the stream supplied using an extraction solvent, may be selectively extracted and separated as a lower portion. For example, the extraction solvent may include one or more selected from the group consisting of sulfolane, alkylsulfolane, N-formyl morpholine, N-methyl pyrrolidone, tetraethylene glycol, triethylene glycol, and diethylene glycol. In addition, the extraction solvent may further include water as a co-solvent.

A separately required device may be further included at a rear end of the first extractive distillation column ($1^{st}$ EDC). For example, the lower discharge stream from the first extractive distillation column ($1^{st}$ EDC) may include the extraction solvent together with the aromatic hydrocarbons as an extract. Therefore, the lower discharge stream from the first extractive distillation column ($1^{st}$ EDC) is subjected to a separate solvent recovery column to be separated into the extraction solvent and the aromatic hydrocarbons.

According to the exemplary embodiment of the present invention, one or more benzene separation columns (BZ) may be further included. Specifically, the lower discharge stream from the first extractive distillation column ($1^{st}$ EDC) or the lower discharge stream from the first extractive distillation column ($1^{st}$ EDC) and the discharge stream from a dialkylation reaction unit (HDA) may be subjected to one or more benzene separation columns (BZ), thereby separating benzene from the lower discharge stream of the first extractive distillation column ($1^{st}$ EDC) or the lower discharge stream of the first extractive distillation column ($1^{st}$ EDC) and the discharge stream from the hydrodealkylation reaction unit (HDA).

According to the exemplary embodiment of the present invention, a toluene separation column (TOL) may be further included. Specifically, while being subjected to the one or more benzene separation columns (BZ), a stream including C7+ aromatic hydrocarbons remaining after separating benzene, for example, the lower discharge stream from the benzene separation column (BZ), may be supplied to the toluene separation column (TOL). Here, a C7 aromatic hydrocarbon and C8+ aromatic hydrocarbons may be separated in the toluene separation column (TOL). For example, the upper discharge stream from the toluene separation column (TOL) including a C7 aromatic hydrocarbon may be supplied to the dialkylation reaction unit (HDA) or separately separated to produce toluene. In addition, the lower discharge stream from the toluene separation column (TOL) including C8+ aromatic hydrocarbons may be separated and used as a fuel, or removed.

According to an exemplary embodiment of the present invention, the C8 separation column (DeC8) may be supplied with the lower discharge stream from the C7 separation column (DeC7) including C8+ hydrocarbons and separated into an upper discharge stream including a C8 hydrocarbon and a lower discharge stream including C9+ hydrocarbons. Here, the upper discharge stream from the C8 separation column (DeC8) including a C8 hydrocarbon may be supplied to the second extractive distillation column ($2^{nd}$ EDC) and subjected to an extraction process, and the lower discharge stream from the C8 separation column (DeC8) including C9+ hydrocarbons may be removed by being discharged to the outside to remove an unnecessary process in which components which are not required in the BTX production process are hydrodesulfurized and removed after separation.

According to an exemplary embodiment of the present invention, the second extractive distillation column ($2^{nd}$ EDC) may separate aromatic hydrocarbons and vinyl aromatic hydrocarbons from the upper discharge stream from the C8 separation column (DeC8) using the extraction solvent. Specifically, in the second extractive distillation column ($2^{nd}$ EDC), the C8 vinyl aromatic hydrocarbon in the upper discharge stream from the C8 separation column (DeC8) may be selectively extracted to be separated as the lower portion of the second extractive distillation column ($2^{nd}$ EDC), and the C8 aromatic hydrocarbon may be separated from the upper portion of the second extractive distillation column ($2^{nd}$ EDC). Here, the extraction solvent may include, for example, one or more selected from the group consisting of, for example, sulfolane, alkyl-sulfolane, N-formyl morpholine, N-methyl pyrrolidone, tetraethylene glycol, triethylene glycol, and diethylene glycol. In addition, the extraction solvent may further include water as a co-solvent.

In addition, the upper discharge stream from the second extractive distillation column ($2^{nd}$ EDC) is a stream including a C8 aromatic hydrocarbon abundant in xylene, and may be supplied to a hydrodealkylation reaction unit (HDA) and subjected to a dialkylation reaction to produce benzene or subjected to the second gasoline hydrogenation unit ($2^{nd}$ GHT) to produce xylene.

A separately required device may be further included at a rear end of the second extractive distillation column ($2^{nd}$ EDC). For example, the lower discharge stream from the second extractive distillation column ($2^{nd}$ EDC) may include the extraction solvent together with the C8 vinyl aromatic hydrocarbon as an extract. Therefore, the lower discharge stream from the second extractive distillation column ($2^{nd}$ EDC) may be subjected to a separate solvent recovery column to be separated into the extraction solvent and the C8 vinyl aromatic hydrocarbon, thereby separating the C8 vinyl aromatic hydrocarbon, that is, styrene.

According to an exemplary embodiment of the present invention, the second gasoline hydrogenation unit ($2^{nd}$ GHT) may hydrogenate olefins and sulfur remaining in the upper discharge stream from the second extractive distillation column ($2^{nd}$ EDC) to remove the olefins and sulfur, and may directly produce xylene (MX) from the upper discharge stream of the second extractive distillation column ($2^{nd}$ EDC) which has passed through the second gasoline hydrogenation unit ($2^{nd}$ GHT).

Hydrogen and a catalyst are separately supplied to the second gasoline hydrogenation unit ($2^{nd}$ GHT), and a gasoline hydrogenation process step to perform hydrodesulfurization in the presence of hydrogen and the catalyst may be carried out. The catalyst may be a catalyst allowing selective hydrogenation. For example, the catalyst may include one or more selected from the group consisting of palladium, platinum, copper, and nickel. In some cases, the catalyst may be supported on one or more supporters selected from the group consisting of gamma alumina, activated carbon, and zeolite.

Unlike the first gasoline hydrogenation unit ($1^{st}$ GHT), the second gasoline hydrogenation unit ($2^{nd}$ GHT) does not include the two gasoline hydrogenation reactors and includes only a third gasoline hydrogenation reactor, thereby decreasing a plant size and minimizing energy use. Specifically, the upper discharge stream from the second extractive distillation column ($2^{nd}$ EDC) supplied to the third gasoline hydrogenation reactor includes a C8 aromatic hydrocarbon abundant in xylene and hardly contains olefins such as diolefin and styrene, thereby omitting a hydrogenation reaction to remove olefins by the liquid phase reaction at a low temperature. For example, the content of the olefins contained in the upper discharge stream from the second extractive distillation column ($2^{nd}$ EDC) may be 0.1 wt % or less or 0.01 wt % to 0.1 wt %.

Specifically, the upper discharge stream from the second extractive distillation column ($2^{nd}$ EDC) is directly supplied to the third gasoline hydrogenation reactor, and the hydrogenation reaction may be carried out at a temperature of 250° C. to 400° C., 280° C. to 360° C., or 280° C. to 320° C. in the third gasoline hydrogenation reactor. The third gasoline hydrogenation reactor is operated at a temperature in the above ranges, thereby performing the hydrogenation reaction in a gas phase. Specifically, in the third gasoline hydrogenation reactor, the olefins remaining in the upper discharge stream from the second extractive distillation column ($2^{nd}$ EDC) are removed, and the hydrogenation reaction may be performed in a gaseous phase to remove sulfur. Thus, a C8 aromatic hydrocarbon abundant in xylene from which olefins and sulfur are removed is discharged from the second gasoline hydrogenation reactor, and xylene (MX) may be produced without additional separation from the discharge stream from the third gasoline hydrogenation reactor.

However, even in the case in which the conventional benzene production process or the BTX production process and the styrene extractive distillation process are theoretically combined, the stream including a C8 aromatic hydrocarbon separated from the styrene extractive distillation process, that is, the upper discharge stream from the second extractive distillation column ($2^{nd}$ EDC) will be supplied to the first gasoline hydrogenation unit ($1^{st}$ GHT) together with the upper discharge stream from the C7 separation column (DeC7).

When the upper discharge stream from the second extractive distillation column ($2^{nd}$ EDC) is supplied to the first gasoline hydrogenation unit ($1^{st}$ GHT) as a raw material of the benzene or BTX production process together with the upper discharge stream of the C7 separation column (DeC7), the amount of hydrogen used increases and a catalyst lifetime decreases due to an increase in a flow rate supplied to the first gasoline hydrogenation unit ($1^{st}$ GHT). In addition, though the upper discharge stream from the second extractive distillation column ($2^{nd}$ EDC) does not include olefins, it is subjected to both the first gasoline hydrogenation reactor and the second gasoline hydrogenation reactor of the first gasoline hydrogenation unit ($1^{st}$ GHT), resulting in unnecessary energy use. In addition, since the stream discharged from the first gasoline hydrogenation unit ($1^{st}$ GHT) includes a C8 aromatic hydrocarbon together with a C6 aromatic hydrocarbon and a C7 aromatic hydrocarbon, a plurality of separation columns for separating the C8 aromatic hydrocarbon is needed at a rear end of the discharge stream from the first gasoline hydrogenation unit ($1^{st}$ GHT), and the stream is subjected to the hydrodealkylation reaction unit (HDA) again or subjected to the xylene separation column (MX) and then mixed with a stream including a C6 aromatic hydrocarbon, which complicates the process.

According to an exemplary embodiment of the present invention, the hydrodealkylation reaction unit (HDA) may be supplied with any one or more of the upper discharge stream from the C7 separation column (DeC7), the upper discharge stream from the second extractive distillation column ($2^{nd}$ EDC), and the upper discharge stream from the toluene separation column (TOL) and a dealkylation reaction may be performed. For example, in the stream supplied to the hydrodealkylation reaction unit (HDA), C7 and C8 hydrocarbons may be included.

The dealkylation reaction may be a reaction of adding hydrogen to aromatic hydrocarbons including an alkyl group to release the alkyl group from a benzene ring. In addition, because a hydrodesulfurization reaction together with the dealkylation reaction occurs in the hydrodealkylation reaction unit (HDA), an unsaturated hydrocarbon may be converted into a saturated hydrocarbon. As a result, a C6 aromatic hydrocarbon, that is, benzene may be produced by the dealkylation reaction.

According to an exemplary embodiment of the present invention, the apparatus for producing aromatic hydrocarbons may be selectively operated in a first mode, a second mode, or a third mode.

The first mode, the second mode, and the third mode may be performed by controlling the operation of some devices in the process or controlling a flow in the process. Specifically, during the operation in the first mode, the hydrodealkylation reaction unit (HDA) may stop being operated. Here, piping between the C7 separation column (DeC7) and the hydrodealkylation reaction unit (HDA) may be closed and piping between the C7 separation column (DeC7) and the first gasoline hydrogenation unit ($1^{st}$ GHT) may be opened. Closing and opening of the piping may be performed by a separate device such as a valve. Therefore, during the operation in the first mode, the upper discharge stream from the C7 separation column (DeC7) may not be supplied to the hydrodealkylation reaction unit (HDA) but supplied to the first gasoline hydrogenation unit ($1^{st}$ GHT).

In addition, the second gasoline hydrogenation unit ($2^{nd}$ GHT) may be operated in the first mode. Here, piping between the second extractive distillation column ($2^{nd}$ EDC) and the hydrodealkylation reaction unit (HDA) may be closed and piping between the second extractive distillation column ($2^{nd}$ EDC) and the second gasoline hydrogenation unit ($2^{nd}$ GHT) may be opened. Therefore, during the operation in the first mode, the upper discharge stream from the second extractive distillation column ($2^{nd}$ EDC) may not be supplied to the hydrodealkylation reaction unit (HDA) but may be supplied to the second gasoline hydrogenation unit ($2^{nd}$ GHT).

During the first mode of operation, BTX may be produced together with styrene. Specifically, benzene and toluene may be separated from the discharge stream from the first gasoline hydrogenation unit ($1^{st}$ GHT), xylene may be separated from the discharge stream from the second gasoline hydrogenation unit ($2^{nd}$ GHT), and styrene may be separated from the lower discharge stream from the second extractive distillation column ($2^{nd}$ EDC).

More specifically, during the operation in the first mode, the upper discharge stream from the C7 separation column (DeC7) may be supplied to the first gasoline hydrogenation unit ($1^{st}$ GHT) together with the upper discharge stream from the C6 separation column (DeC6), and the discharge stream of the first gasoline hydrogenation unit ($1^{st}$ GHT) includes a C6 aromatic hydrocarbon and a C7 aromatic hydrocarbon. The discharge stream from the first gasoline hydrogenation unit ($1^{st}$ GHT) is directly supplied to the first extractive distillation column ($1^{st}$ EDC), the first extractive distillation column ($1^{st}$ EDC) separates non-aromatic hydrocarbons as an upper portion and benzene (BZ) and toluene (TOL) as a lower discharge stream including the C6 aromatic hydrocarbon and the C7 aromatic hydrocarbon. In addition, the upper discharge stream from the second extractive distillation column ($2^{nd}$ EDC) is a stream including a C8 aromatic hydrocarbon and is supplied to the second gasoline hydrogenation unit ($2^{nd}$ GHT), and in the second gasoline hydrogenation unit ($2^{nd}$ GHT), may be subjected to a hydrodesulfurization reaction to produce xylene (MX). In addition, the lower discharge stream from the second extractive distillation column ($2^{nd}$ EDC) is a stream including a C8 aromatic hydrocarbon abundant in styrene, and styrene (SM) may be separated after removing a solvent in a solvent recovery column. As such, when operated in the first mode, styrene and BTX may be produced at simultaneously.

In addition, the hydrodealkylation reaction unit (HDA) may be operated in the second mode. Here, piping between the C7 separation column (DeC7) and the hydrodealkylation reaction unit (HDA) may be opened and piping between the C7 separation column (DeC7) and the first gasoline hydrogenation unit ($1^{st}$ GHT) may be closed. Therefore, in the second mode, the upper discharge stream from the C7 separation column (DeC7) may not be supplied to the first gasoline hydrogenation unit ($1^{st}$ GHT) but supplied to the hydrodealkylation reaction unit (HDA).

In addition, in the second mode, the second gasoline hydrogenation unit ($2^{nd}$ GHT) may stop being operated. Here, piping between the second extractive distillation column ($2^{nd}$ EDC) and the hydrodealkylation reaction unit (HDA) may be opened and piping between the second extractive distillation column ($2^{nd}$ EDC) and the second gasoline hydrogenation unit ($2^{nd}$ GHT) may be closed. Therefore, in the second mode, the upper discharge stream from the second extractive distillation column ($2^{nd}$ EDC) may not be supplied to the second gasoline hydrogenation unit ($2^{nd}$ GHT) but supplied to the hydrodealkylation reaction unit (HDA).

During the second mode of operation, benzene may be produced together with styrene. Specifically benzene may be separated from the discharge stream from the first gasoline hydrogenation unit ($1^{st}$ GHT) and the discharge stream from the hydrodealkylation reaction unit (HDA), and styrene may be separated from the lower discharge stream from the second extractive distillation column ($2^{nd}$ EDC).

More specifically, in the second mode, the upper discharge stream from the C6 separation column (DeC6) is supplied to the first gasoline hydrogenation unit ($1^{st}$ GHT), and the discharge stream from the first gasoline hydrogenation unit ($1^{st}$ GHT) includes a C6 aromatic hydrocarbon. The discharge stream from the first gasoline hydrogenation unit ($1^{st}$ GHT) may be directly supplied to the first extractive distillation column ($1^{st}$ EDC). Non-aromatic hydrocarbons may be separated as an upper portion of the first extractive distillation column ($1^{st}$ EDC), and a lower discharge stream of the first extractive distillation column ($1^{st}$ EDC) including a C6 aromatic hydrocarbon may be supplied to the benzene separation column (BZ) with the discharge stream from the hydrodealkylation reaction unit (HDA) including the C6 aromatic hydrocarbon to separate benzene. Here, the lower discharge stream from the first extractive distillation column ($1^{st}$ EDC) and the discharge stream from the hydrodealkylation reaction unit (HDA) may be supplied to the benzene separation column (BZ) as individual streams, or may be supplied to the benzene separation column (BZ) as a mixed stream. In addition, the lower discharge stream from the second extractive distillation column ($2^{nd}$ EDC) is a stream including a C8 aromatic hydrocarbon, that is, styrene and an extraction solvent, and styrene (SM) may be separated after removing the solvent in a solvent recovery column. As such, styrene and benzene may be produced at the same time in the second mode.

In addition, the hydrodealkylation reaction unit (HDA) may be operated during the third mode of operation. Here, piping between the C7 separation column (DeC7) and the hydrodealkylation reaction unit (HDA) may be opened and piping between the C7 separation column (DeC7) and the first gasoline hydrogenation unit ($1^{st}$ GHT) may be closed. Therefore, in the third mode, the upper discharge stream from the C7 separation column (DeC7) may not be supplied to the first gasoline hydrogenation unit ($1^{st}$ GHT) but supplied to the hydrodealkylation reaction unit (HDA).

In addition, in the third mode, the second gasoline hydrogenation unit ($2^{nd}$ GHT) may be operated. Here, piping between the second extractive distillation column ($2^{nd}$ EDC) and the hydrodealkylation reaction unit (HDA) may be closed and piping between the second extractive distillation column ($2^{nd}$ EDC) and the second gasoline hydrogenation unit ($2^{nd}$ GHT) may be opened. Therefore, in the third mode, the upper discharge stream from the second extractive distillation column ($2^{nd}$ EDC) may not be supplied to the hydrodealkylation reaction unit (HDA) but supplied to the second gasoline hydrogenation unit ($2^{nd}$ GHT).

During the third mode of operation, benzene and xylene may be produced together with styrene. Specifically, benzene may be separated from the discharge stream of the first gasoline hydrogenation unit ($1^{st}$ GHT) and the discharge stream of the hydrodealkylation reaction unit (HDA), xylene may be separated from the discharge stream of the second gasoline hydrogenation unit ($2^{nd}$ GHT), and styrene may be separated from the lower discharge stream of the second extractive distillation column ($2^{nd}$ EDC).

More specifically, in the third mode, the upper discharge stream from the C6 separation column (DeC6) is supplied to the first gasoline hydrogenation unit ($1^{st}$ GHT), and the discharge stream from the first gasoline hydrogenation unit ($1^{st}$ GHT) includes a C6 aromatic hydrocarbon. The discharge stream from the first gasoline hydrogenation unit ($1^{st}$ GHT) may be directly supplied to the first extractive distillation column ($1^{st}$ EDC), and non-aromatic hydrocarbons may be separated as an upper portion in the first extractive distillation column ($1^{st}$ EDC), and a lower discharge stream including a C6 aromatic hydrocarbon may be supplied to the benzene separation column (BZ) with the discharge stream from the hydrodealkylation reaction unit (HDA) including the C6 aromatic hydrocarbon to separate benzene. Here, the lower discharge stream from the first extractive distillation column ($1^{st}$ EDC) and the discharge stream from the hydrodealkylation reaction unit (HDA) may be supplied to the benzene separation column (BZ) as individual streams, or may be supplied to the benzene separation column (BZ) as a mixed stream. In addition, the upper discharge stream from the second extractive distillation column ($2^{nd}$ EDC) is a stream including a C8 aromatic hydrocarbon and is supplied to the second gasoline hydrogenation unit ($2^{nd}$ GHT), and may be subjected to a hydrodesulfurization reaction in the second gasoline hydrogenation unit ($2^{nd}$ GHT) to produce xylene (MX). In addition, the lower discharge stream from the second extractive distillation column ($2^{nd}$ EDC) is a stream including a C8 aromatic hydrocarbon, that is, styrene and an extraction solvent, and styrene (SM) may be separated after removing the solvent in a solvent recovery column. As such, in the third mode, benzene and xylene may be produced simultaneously with styrene.

According to an exemplary embodiment of the present invention, in the apparatus for producing aromatic hydrocarbons, if necessary, devices such as a distillation column (not shown), a condenser (not shown), a reboiler (not shown), a valve (not shown), a pump (not shown), a separator (not shown), and a mixer (not shown) may be further installed.

Hereinabove, the apparatus for producing aromatic hydrocarbons according to the present invention has been described and illustrated in the drawings, but the description and the illustration in the drawings are of the core components, and intended for understanding of the present invention. In addition to the process and apparatus described above and illustrated in the drawings, the process and the apparatus which are not described and illustrated separately may be appropriately applied and used for carrying out the apparatus for producing aromatic hydrocarbons according to the present invention.

Hereinafter, the present invention will be described in more detail by the Examples. However, the following Examples are provided for illustrating the present invention. It would be apparent to a person skilled in the art that various modifications and alterations may be made without departing from the scope and spirit of the present invention, and the scope of the present invention is not limited thereto.

EXAMPLES

Example 1

A first mode (thick solid line) process illustrated in FIG. 1 was simulated in an Aspen Plus simulator available from Aspen Technology Inc.

Specifically, a raw material stream including C5 to C10 hydrocarbons was supplied to a C6 separation column (DeC6) and a raw material stream including C5 and C6 hydrocarbons but no styrene was supplied to a first gasoline hydrogenation unit ($1^{st}$ GHT).

An upper discharge stream from the C6 separation column (DeC6) including C6– hydrocarbons was supplied to the first gasoline hydrogenation unit ($1^{st}$ GHT), and a lower discharge stream including C7+ hydrocarbons was supplied to a C7 separation column (DeC7). In addition, in the C7 separation column (DeC7), an upper discharge stream including a C7 hydrocarbon was supplied to the first gasoline hydrogenation unit (1$^{st}$ GHT), and a lower discharge stream including C8+ hydrocarbons was supplied to a C8 separation column (DeC8).

The upper discharge stream from the C6 separation column (DeC6) including C6− hydrocarbons and the upper discharge stream from the C7 separation column (DeC7) including a C7 hydrocarbon were supplied to the first gasoline hydrogenation unit (1$^{st}$ GHT), and a total amount of the discharge stream from the first gasoline hydrogenation unit (1$^{st}$ GHT) including the C6 aromatic hydrocarbon and the C7 aromatic hydrocarbon was supplied to the first extractive distillation column (1$^{st}$ EDC).

The lower discharge stream from the first extractive distillation column (1$^{st}$ EDC) included the C6 and C7 aromatic hydrocarbons, but was a stream from which non-aromatic hydrocarbons were removed, and was supplied to a benzene separation column (BZ), and benzene was separated from an upper portion of the benzene separation column (BZ) and the lower discharge stream was supplied to a toluene separation column (TOL). In the toluene separation column (TOL), toluene was separated from the upper portion and a heavy substance including C8+ hydrocarbons was separated from the lower portion and removed.

The lower discharge stream from the C7 separation column (DeC7) including C8+ hydrocarbons was supplied to the C8 separation column (DeC8), in the C8 separation column (DeC8), the lower discharge stream including C9+ hydrocarbons was discharged to the outside and removed, and the upper discharge stream from the C8 separation column (DeC8) including a C8 hydrocarbon was supplied to a second extractive distillation column (2$^{nd}$ EDC).

The lower discharge stream from the second extractive distillation column (2$^{nd}$ EDC) included styrene and was supplied to a solvent recovery column to remove a solvent and then styrene was separated.

In addition, the upper discharge stream from the second extractive distillation column (2$^{nd}$ EDC) was a stream abundant in xylene and was supplied to a second gasoline hydrogenation unit (2$^{nd}$ GHT), and xylene was produced from the discharge stream from the second gasoline hydrogenation unit (2$^{nd}$ GHT).

A flow rate (ton/hr) of the stream the simulated process flow is shown in Table 1. In addition, a total amount of steam used in the process was measured as a total amount of energy used in the process, and is shown in Table 2, as a criterion (100.0) for a total amount of steam used in the other Examples and Comparative Examples.

Example 2

The second mode (dotted line) process illustrated in FIG. 1 was simulated using an Aspen Plus simulator available from Aspen Technology Inc.

Specifically, a raw material stream including C5 to C10 hydrocarbons was supplied to the C6 separation column (DeC6) and a raw material stream including C5 and C6 hydrocarbons but no styrene was supplied to the first gasoline hydrogenation unit (1$^{st}$ GHT).

An upper discharge stream from the C6 separation column (DeC6) including C6− hydrocarbons was supplied to the first gasoline hydrogenation unit (1$^{st}$ GHT), and a lower discharge stream including C7+ hydrocarbons was supplied to the C7 separation column (DeC7). In addition, in the C7 separation column (DeC7), an upper discharge stream including a C7 hydrocarbon was supplied to the hydrodealkylation reaction unit (HDA), and a lower discharge stream including C8+ hydrocarbons was supplied to the C8 separation column (DeC8).

The upper discharge stream from the C6 separation column (DeC6) including C6− hydrocarbons was supplied to the first gasoline hydrogenation unit (1$^{st}$ GHT), and a total amount of the discharge stream from the first gasoline hydrogenation unit (1$^{st}$ GHT) including the C6 aromatic hydrocarbon was supplied to the first extractive distillation column (1$^{st}$ EDC).

The lower discharge stream from the first extractive distillation column (1$^{st}$ EDC) included the C6 aromatic hydrocarbons, but was a stream from which non-aromatic hydrocarbons were removed, and was supplied to the benzene separation column (BZ) with the discharge stream from the hydrodealkylation reaction unit (HDA), and benzene was separated from an upper portion of the benzene separation column (BZ) and the lower discharge stream was supplied to the toluene separation column (TOL). In the toluene separation column (TOL), the C7 aromatic hydrocarbon was separated from the upper portion and supplied to the hydrodealkylation reaction unit (HDA), and a heavy substance including the C8+ hydrocarbons was separated from the lower portion and removed.

The lower discharge stream from the C7 separation column (DeC7) including the C8+ hydrocarbons was supplied to the C8 separation column (DeC8), in the C8 separation column (DeC8), the lower discharge stream including C9+ hydrocarbons was discharged to the outside and removed, and the upper discharge stream from the C8 separation column (DeC8) including a C8 hydrocarbon was supplied to the second extractive distillation column (2$^{nd}$ EDC).

The lower discharge stream from the second extractive distillation column (2$^{nd}$ EDC) included styrene and was supplied to the solvent recovery column to remove a solvent and then styrene was separated.

In addition, the upper discharge stream from the second extractive distillation column (2$^{nd}$ EDC) included the C8 aromatic hydrocarbon and was supplied to the hydrodealkylation reaction unit (HDA), and benzene was produced from the discharge stream from the hydrodealkylation reaction unit (HDA).

A flow rate (ton/hr) of the stream of the simulated process flow is shown in Table 1. In addition, a total amount of steam used in the process was measured as a total amount of energy used in the process relative to the amount of steam used in Example 1, and is shown in Table 2.

Example 3

A third mode (thick dotted line) process illustrated in FIG. 1 was simulated using an Aspen Plus simulator available from Aspen Technology Inc.

Specifically, a raw material stream including C5 to C10 hydrocarbons was supplied to the C6 separation column (DeC6) and a raw material stream including C5 and C6 hydrocarbons but no styrene was supplied to the first gasoline hydrogenation unit (1$^{st}$ GHT).

An upper discharge stream from the C6 separation column (DeC6) including C6− hydrocarbons was supplied to the first gasoline hydrogenation unit (1$^{st}$ GHT), and a lower discharge stream including C7+ hydrocarbons was supplied to the C7 separation column (DeC7). In addition, in the C7 separation column (DeC7), an upper discharge stream including a C7 hydrocarbon was supplied to the hydrodealkylation reaction unit (HDA), and a lower discharge stream including C8+ hydrocarbons was supplied to the C8 separation column (DeC8).

The upper discharge stream from the C6 separation column (DeC6) including C6− hydrocarbons was supplied to the first gasoline hydrogenation unit ($1^{st}$ GHT), and a total amount of the discharge stream from the first gasoline hydrogenation unit ($1^{st}$ GHT) including the C6 aromatic hydrocarbon was supplied to the first extractive distillation column ($1^{st}$ EDC).

The lower discharge stream from the first extractive distillation column ($1^{st}$ EDC) included the C6 aromatic hydrocarbons, but was a stream from which non-aromatic hydrocarbons were removed, and was supplied to the benzene separation column (BZ) with the discharge stream from the hydrodealkylation reaction unit (HDA), and benzene was separated from an upper portion of the benzene separation column (BZ) and the lower discharge stream was supplied to the toluene separation column (TOL). In the toluene separation column (TOL), the C7 aromatic hydrocarbon was separated from the upper portion and supplied to the hydrodealkylation reaction unit (HDA), and a heavy substance including the C8+ hydrocarbons was separated from the lower portion and removed.

The lower discharge stream from the C7 separation column (DeC7) including the C8+ hydrocarbons was supplied to the C8 separation column (DeC8), in the C8 separation column (DeC8), the lower discharge stream including C9+ hydrocarbons was discharged to the outside and removed, and the upper discharge stream from the C8 separation column (DeC8) including a C8 hydrocarbon was supplied to the second extractive distillation column ($2^{nd}$ EDC).

The lower discharge stream from the second extractive distillation column ($2^{nd}$ EDC) included styrene and was supplied to the solvent recovery column to remove a solvent and then styrene was separated.

In addition, the upper discharge stream from the second extractive distillation column ($2^{nd}$ EDC) was a stream abundant in xylene and was supplied to a second gasoline hydrogenation unit ($2^{nd}$ GHT), and xylene was produced from the discharge stream from the second gasoline hydrogenation unit ($2^{nd}$ GHT).

A flow rate (ton/hr) of the stream of the simulated process flow is shown in Table 1. In addition, a total amount of steam used in the process was measured as a total amount of energy used in the process relative to the amount of steam used in Example 1, and is shown in Table 2.

Comparative Example

Comparative Example 1

A first mode (thick solid line) process illustrated in FIG. 2 was simulated using an Aspen Plus simulator available from Aspen Technology Inc.

Specifically, a raw material stream including C5 to C10 hydrocarbons was supplied to the C7 separation column (DeC7) and a raw material stream including C5 and C6 hydrocarbons but no styrene was supplied to the first gasoline hydrogenation unit ($1^{st}$ GHT).

An upper discharge stream from the C7 separation column (DeC7) including C7− hydrocarbons was supplied to the first gasoline hydrogenation unit ($1^{st}$ GHT), and a lower discharge stream from the C7 separation column (DeC7) including C8+ hydrocarbons was supplied to the C8 separation column (DeC8).

In the C8 separation column (DeC8), the upper discharge stream from which C9+ hydrocarbons were removed was supplied to the second extractive distillation column ($2^{nd}$ EDC). In the second extractive distillation column ($2^{nd}$ EDC), a stream including a C8 vinyl aromatic hydrocarbon was separated from the lower discharge stream and supplied to the solvent recovery column, and in the solvent recovery column, styrene from which the solvent was removed was separated. In addition, the upper discharge stream from the second extractive distillation column ($2^{nd}$ EDC) was a stream including a C8 aromatic hydrocarbon and supplied to the first gasoline hydrogenation unit ($1^{st}$ GHT) with the upper discharge stream from the C7 separation column (DeC7).

The discharge stream from the first gasoline hydrogenation unit ($1^{st}$ GHT) included C6 to C8 aromatic hydrocarbons and was supplied to the C6 separation column (DeC6). In the C6 separation column (DeC6), the stream was separated into an upper discharge stream including a C6 aromatic hydrocarbon and a lower discharge stream including C7 and C8 aromatic hydrocarbons, and the upper discharge stream was supplied to the first extractive distillation column ($1^{st}$ EDC) and the lower discharge stream was supplied to a xylene separation column (MX).

A lower discharge stream from the first extractive distillation column ($1^{st}$ EDC) was subjected to the benzene separation column (BZ) and the toluene separation column (TOL) to separate benzene and toluene, and the remaining stream was supplied to the xylene separation column (MX).

In the xylene separation column (MX), an upper discharge stream including a C7 aromatic hydrocarbon was supplied to the first extractive distillation column ($1^{st}$ EDC) with an upper discharge stream from the C6 separation column (DeC6), and xylene was produced from the lower discharge stream.

A flow rate (ton/hr) of the stream of the simulated process flow is shown in Table 1. In addition, a total amount of steam used in the process was measured as a total amount of energy used in the process relative to the amount of steam used in Example 1, and is shown in Table 2.

Comparative Example 2

A second mode (dotted line) process illustrated in FIG. 2 was simulated using an Aspen Plus.

Specifically, a raw material stream including C5 to C10 hydrocarbons was supplied to the C7 separation column (DeC7) and a raw material stream including C5 and C6 hydrocarbons but no styrene was supplied to the first gasoline hydrogenation unit ($1^{st}$ GHT).

An upper discharge stream from the C7 separation column (DeC7) including C7− hydrocarbons was supplied to the first gasoline hydrogenation unit ($1^{st}$ GHT), and a lower discharge stream from the C7 separation column (DeC7) including C8+ hydrocarbons was supplied to the C8 separation column (DeC8).

In the C8 separation column (DeC8), the upper discharge stream from which C9+ hydrocarbons were removed was supplied to the second extractive distillation column ($2^{nd}$ EDC). In the second extractive distillation column ($2^{nd}$ EDC), a stream including a C8 vinyl aromatic hydrocarbon was separated from the lower discharge stream and supplied to the solvent recovery column, and in the solvent recovery column, styrene from which the solvent was removed was separated. In addition, the upper discharge stream from the second extractive distillation column ($2^{nd}$ EDC) was a stream including a C8 aromatic hydrocarbon and supplied to the first gasoline hydrogenation unit (1$^{st}$ GHT) with the upper discharge stream from the C7 separation column (DeC7).

The discharge stream from the first gasoline hydrogenation unit (1$^{st}$ GHT) included C6 to C8 aromatic hydrocarbons and was supplied to the C6 separation column (DeC6). In the C6 separation column (DeC6), the stream was separated into an upper discharge stream including a C6 aromatic hydrocarbon and a lower discharge stream including C7+ aromatic hydrocarbons, and the upper discharge stream was supplied to the first extractive distillation column (1$^{st}$ EDC) and the lower discharge stream was supplied to the hydrodealkylation reaction unit (HDA).

A lower discharge stream from the first extractive distillation column (1$^{st}$ EDC) and a discharge stream from the hydrodealkylation reaction unit (HDA) were subjected to the benzene separation column (BZ) to separate benzene, the lower discharge stream was supplied to the toluene separation column (TOL). In the toluene separation column (TOL), the C7 aromatic hydrocarbon was separated from the upper portion and supplied to the hydrodealkylation reaction unit (HDA), and a heavy substance including the C8+ hydrocarbons was separated from the lower portion and removed.

A flow rate (ton/hr) of the stream of the simulated process flow is shown in Table 1. In addition, a total amount of steam used in the process was measured as a total amount of energy used in the process relative to the amount of steam used in Example 1, and is shown in Table 2.

Comparative Example 3

A third mode (thick dotted line) process illustrated in FIG. 2 was simulated using an Aspen Plus simulator available from Aspen Technology Inc.

Specifically, a raw material stream including C5 to C10 hydrocarbons was supplied to the C7 separation column (DeC7) and a raw material stream including C5 and C6 hydrocarbons but no styrene was supplied to the first gasoline hydrogenation unit (1$^{st}$ GHT).

An upper discharge stream from the C7 separation column (DeC7) including C7− hydrocarbons was supplied to the first gasoline hydrogenation unit (1$^{st}$ GHT), and a lower discharge stream from the C7 separation column (DeC7) including C8+ hydrocarbons was supplied to the C8 separation column (DeC8).

In the C8 separation column (DeC8), the upper discharge stream from which C9+ hydrocarbons were removed was supplied to the second extractive distillation column (2$^{nd}$ EDC). In the second extractive distillation column (2$^{nd}$ EDC), a stream including a C8 vinyl aromatic hydrocarbon was separated from the lower discharge stream and supplied to the solvent recovery column, and in the solvent recovery column, styrene from which the solvent was removed was separated. In addition, the upper discharge stream from the second extractive distillation column (2nd EDC) was a stream including a C8 aromatic hydrocarbon and supplied to the first gasoline hydrogenation unit (1$^{st}$ GHT) with the upper discharge stream from the C7 separation column (DeC7).

The discharge stream from the first gasoline hydrogenation unit (1$^{st}$ GHT) included C6 to C8 aromatic hydrocarbons and was supplied to the C6 separation column (DeC6). In the C6 separation column (DeC6), the stream was separated into an upper discharge stream including a C6 aromatic hydrocarbon and a lower discharge stream including C7+ aromatic hydrocarbons, and the upper discharge stream was supplied to the first extractive distillation column (1$^{st}$ EDC) and the lower discharge stream was supplied to the xylene separation column (MX).

In the xylene separation column (MX), the upper discharge stream including a C7 aromatic hydrocarbon was supplied to the hydrodealkylation reaction unit (HDA), and xylene was produced from the lower discharge stream.

A lower discharge stream from the first extractive distillation column (1$^{st}$ EDC) and a discharge stream from the hydrodealkylation reaction unit (HDA) were subjected to the benzene separation column (BZ) to separate benzene, and the lower discharge stream was supplied to the toluene separation column (TOL). In the toluene separation column (TOL), the C7 aromatic hydrocarbon was separated from the upper portion and supplied to the hydrodealkylation reaction unit (HDA), and a heavy substance including the C8+ hydrocarbons was separated from the lower portion and removed.

A flow rate (ton/hr) of the stream of the simulated process flow is shown in Table 1. In addition, a total amount of steam used in the process was measured as a total amount of energy used in the process relative to the amount of steam used in Example 1, and is shown in Table 2.

TABLE 1

|  | Example 1 | Example 2 | Example 3 | Comparative Example 1 | Comparative Example 2 | Comparative Example 3 |
| --- | --- | --- | --- | --- | --- | --- |
| S1 | 20.4 | 20.4 | 20.4 | 20.4 | 20.4 | 20.4 |
| S2 | 156 | 156 | 156 | 156.0 | 156 | 156 |
| S11 | 99.1 | 74.3 | 74.3 | 99.1 | 74.3 | 74.3 |
| S12 | 69.6 | 49.2 | 49.2 | 69.6 | 49.2 | 49.2 |
| S13 | 44.6 | 68.2 | 61 | 44.6 | 68.2 | 61.0 |
| S14 | 24 | N/A | N/A | 24.0 | N/A | N/A |
| S20 | 88.6 | 88.6 | 88.6 | N/A | N/A | N/A |
| S21 | 67.4 | 67.4 | 67.4 | N/A | N/A | N/A |
| S22 | 22.6 | N/A | N/A | 111.2 | 111.2 | 111.2 |
| S23 | 44.9 | 44.9 | 44.9 | 44.9 | 44.9 | 44.9 |
| S24 | 20.4 | 20.4 | 20.4 | 20.4 | 20.4 | 20.4 |
| S25 | 24.5 | 24.5 | 24.5 | 24.5 | 24.5 | 24.5 |
| S26 | 10.4 | 10.4 | 10.4 | 10.4 | 10.4 | 10.4 |
| S27 | 10 | N/A | N/A | N/A | N/A | N/A |
| S28 | 10 | N/A | N/A | N/A | N/A | N/A |
| S29 | N/A | N/A | N/A | 10.0 | 10.0 | 10.0 |
| S30 | N/A | 22.6 | N/A | N/A | N/A | N/A |
| S31 | N/A | 10.0 | N/A | N/A | N/A | N/A |
| S32 | N/A | 6.9 | N/A | N/A | N/A | N/A |

TABLE 1-continued

|  | Example 1 | Example 2 | Example 3 | Comparative Example 1 | Comparative Example 2 | Comparative Example 3 |
|---|---|---|---|---|---|---|
| S33 | N/A | 33.4 | N/A | N/A | N/A | N/A |
| S40 | N/A | N/A | 22.6 | N/A | N/A | N/A |
| S41 | N/A | N/A | 26.2 | N/A | N/A | N/A |
| S42 | N/A | N/A | 13.1 | N/A | N/A | N/A |
| S43 | N/A | N/A | 10.0 | N/A | N/A | N/A |
| S44 | N/A | N/A | 10.0 | N/A | N/A | N/A |
| S50 | N/A | N/A | N/A | 108.3 | 108.3 | 108.3 |
| S51 | N/A | N/A | N/A | 74.2 | N/A | N/A |
| S52 | N/A | N/A | N/A | 34.1 | N/A | N/A |
| S53 | N/A | N/A | N/A | 25.0 | N/A | N/A |
| S54 | N/A | N/A | N/A | 10.0 | N/A | N/A |
| S55 | N/A | N/A | N/A | 1.0 | N/A | N/A |
| S60 | N/A | N/A | N/A | N/A | 34.1 | N/A |
| S61 | N/A | N/A | N/A | N/A | 6.9 | N/A |
| S62 | N/A | N/A | N/A | N/A | 33.4 | N/A |
| S70 | N/A | N/A | N/A | N/A | N/A | 34.1 |
| S71 | N/A | N/A | N/A | N/A | N/A | 10 |
| S72 | N/A | N/A | N/A | N/A | N/A | 24.0 |
| S73 | N/A | N/A | N/A | N/A | N/A | 13.1 |
| S74 | N/A | N/A | N/A | N/A | N/A | 26.2 |

TABLE 2

|  | Example 1 | Example 2 | Example 3 | Comparative Example 1 | Comparative Example 2 | Comparative Example 3 |
|---|---|---|---|---|---|---|
| Total amount of steam used | 100.0 | 96.5 | 102.8 | 116.9 | 105.6 | 122.0 |

\* Total amount of steam used: Ratio of the total amount of steam used relative to criterion (Example 1: 100.0)

Referring to Tables 1 and 2, the apparatus for producing aromatic hydrocarbons according to the present invention was used and operated in the first mode (Example 1), the second mode (Example 2), or the third mode (Example 3), thereby confirming that BTX, benzene, or benzene and xylene as well as styrene may be selectively produced. In addition, as a result of comparing Example 1 with Comparative Example 1, Example 2 with Comparative Example 2, and Example 3 with Comparative Example 3, when the aromatic hydrocarbon was produced by the method according to the present invention, the final product output was at an equal to superior level.

In addition, as a result of comparing Example 1 with Comparative Example 1, Example 2 with Comparative Example 2, and Example 3 with Comparative Example 3 which were operated in different modes from each other, the total amount of steam used for heating in the process of the Examples was significantly low.

Specifically, in Examples 1 to 3, only C6-hydrocarbons were supplied to the first gasoline hydrogenation unit (1$^{st}$ GHT) and a C7 hydrocarbon was supplied to the first gasoline hydrogenation unit (1$^{st}$ GHT) only when toluene was produced, thereby minimizing the stream supplied to the first gasoline hydrogenation unit (1$^{st}$ GHT) to decrease an amount of hydrogen used, increase a catalyst lifetime, and reduce utility costs. In addition, the C8 aromatic hydrocarbon was supplied to the second gasoline hydrogenation unit (2$^{nd}$ GHT) when xylene was produced, and supplied to the hydrodealkylation reaction unit (HDA) when xylene was not produced, thereby removing unnecessary processes such as separation and mixing using the C6 separation column (DeC6) and the xylene separation column (MX) at a rear end of the first gasoline hydrogenation unit (1$^{st}$ GHT) to decrease an amount of steam used.

In comparison, in Comparative Examples 1 to 3, the C7 hydrocarbon and the C8 aromatic hydrocarbon were supplied to the first gasoline hydrogenation unit (1$^{st}$ GHT) regardless of the mode operation, thereby increasing the stream supplied to the first gasoline hydrogenation unit (1$^{st}$ GHT), and thus, increasing an amount of hydrogen used and decreasing a catalyst lifetime to increase utility costs. In addition, it was found that one or more of the C6 separation column (DeC6) and the xylene separation column (MX) for separating the C6 to C8 hydrocarbons were needed at a rear end of the first gasoline hydrogenation unit (1$^{st}$ GHT), and thus, unnecessary processes such as separation and mixing were required to increase an amount of steam used.

The invention claimed is:

1. An apparatus for producing aromatic hydrocarbons, the apparatus comprising:
    a C6 separation column;
    a C7 separation column;
    a first gasoline hydrogenation unit;
    a C8 separation column;
    an extractive distillation column;
    a hydrodealkylation reaction unit; and
    a second gasoline hydrogenation unit,
    wherein the C6 separation column is supplied with a raw material stream,
    wherein an upper discharge stream of the C6 separation column is supplied to the first gasoline hydrogenation unit, and a lower discharge stream of the C6 separation column is supplied to the C7 separation column,
    wherein an upper discharge stream of the C7 separation column is supplied to the first gasoline hydrogenation unit or the hydrodealkylation reaction unit, and a lower discharge stream of the C7 separation column is supplied to the C8 separation column, wherein a hydrosulfurization reaction is carried out in the first gasoline hydrogenation unit, wherein a lower discharge stream of the C8 separation column is removed, and an upper discharge stream of the C8 separation column is supplied to the extractive distillation column, wherein an upper discharge stream of the extractive distillation column is supplied to the second gasoline hydrogenation unit or the hydrodealkylation reaction unit, wherein a dealkylation reaction is performed in the hydrodealkylation reaction unit, and wherein a dehydrodesulfurization reaction is performed in the second gasoline hydrogenation unit.

2. The apparatus for producing aromatic hydrocarbons of claim 1, wherein the apparatus is operated in a first mode, a second mode, or a third mode, wherein in the first mode, the second gasoline hydrogenation unit is operated and the hydrodealkylation reaction unit is not operated, wherein in the second mode, the hydrodealkylation reaction unit is operated and the second gasoline hydrogenation unit is not operated, and wherein in the third mode, the hydrodealkylation reaction unit and the second gasoline hydrogenation unit are operated.

3. The apparatus for producing aromatic hydrocarbons of claim 2, wherein in the first mode:

a piping between the C7 separation column and the hydrodealkylation reaction unit is closed and a piping between the C7 separation column and the first gasoline hydrogenation unit is opened, and a piping between the extractive distillation column and the hydrodealkylation reaction unit is closed and a piping between the extractive distillation column and the second gasoline hydrogenation unit is opened, wherein the closing and opening of the pipings are performed by one or more valves.

4. The apparatus for producing aromatic hydrocarbons of claim 2, wherein in the second mode:

a piping between the C7 separation column and the hydrodealkylation reaction unit is opened and a piping between the C7 separation column and the first gasoline hydrogenation unit is closed, and a piping between the extractive distillation column and the hydrodealkylation reaction unit is opened and a piping between the extractive distillation column and the second gasoline hydrogenation unit is closed, wherein the closing and opening of the pipings are performed by one or more valves.

5. The apparatus for producing aromatic hydrocarbons of claim 2, wherein in the third mode:

a piping between the C7 separation column and the hydrodealkylation reaction unit is opened and a piping between the C7 separation column and the first gasoline hydrogenation unit is closed, and a piping between the extractive distillation column and the hydrodealkylation reaction unit is closed and a piping between the extractive distillation column and the second gasoline hydrogenation unit is opened, wherein the closing and opening of the pipings are performed by one or more valves.

6. The apparatus for producing aromatic hydrocarbons of claim 2, wherein in the first mode:

benzene and toluene are separated from a discharge stream of the first gasoline hydrogenation unit, xylene is separated from a discharge stream of the second gasoline hydrogenation unit, and styrene is separated from a lower discharge stream of the extractive distillation column.

7. The apparatus for producing aromatic hydrocarbons of claim 2, wherein in the second mode:

benzene is separated from a discharge stream of the first gasoline hydrogenation unit, and styrene is separated from a lower discharge stream from the extractive distillation column.

8. The apparatus for producing aromatic hydrocarbons of claim 2, wherein in the third mode:

benzene is separated from a discharge stream of the first gasoline hydrogenation unit and a discharge stream of the hydrodealkylation reaction unit, xylene is separated from a discharge stream of the second gasoline hydrogenation unit, and styrene is separated from a lower discharge stream of the extractive distillation column.

9. The apparatus for producing aromatic hydrocarbons of claim 1, wherein the raw material stream includes C5 to C10 hydrocarbons.

10. The apparatus for producing aromatic hydrocarbons of claim 1, wherein the first gasoline hydrogenation unit includes a first gasoline hydrogenation reactor and a second gasoline hydrogenation reactor, and wherein an operation temperature of the first gasoline hydrogenation reactor is 50° C. to 200° C. and an operation temperature of the second gasoline hydrogenation reactor is 250° C. to 350° C.

11. The apparatus for producing aromatic hydrocarbons of claim 1, wherein the second gasoline hydrogenation unit includes a third gasoline hydrogenation reactor, and wherein an operation temperature of the third gasoline hydrogenation reactor is 250° C. to 350° C.

12. The apparatus for producing aromatic hydrocarbons of claim 1, wherein the first gasoline hydrogenation unit is separately supplied with a raw material stream including C5 and C6 hydrocarbons, and the raw material stream supplied to the first gasoline hydrogenation unit does not include styrene.

13. The apparatus for producing aromatic hydrocarbons of claim 2, further comprising: a first extractive distillation column supplied with a discharge stream from the first gasoline hydrogenation unit, wherein extractive distillation is performed in the first extractive distillation column.

14. The apparatus for producing aromatic hydrocarbons of claim 13, wherein in the second mode and the third mode, benzene is separated from a lower discharge stream of the first extractive distillation column and a discharge stream from the hydrodealkylation reaction unit.

* * * * *